United States Patent [19]

Noda et al.

[11] Patent Number: 5,017,570

[45] Date of Patent: May 21, 1991

[54] DIBENZOXAZEPINE COMPOUNDS USEFUL IN THE TREATMENT OF CEREBRAL VASOSPASM OR ITS SEQUELA

[75] Inventors: Yukijumi Noda; Makoto Sugawa, both of Tokyo; Akira Kohda, Kanagawa, all of Japan

[73] Assignee: Chugai Seiyaku Kabushiki Kaisha, Tokyo, Japan

[21] Appl. No.: 560,504

[22] Filed: Jul. 24, 1990

Related U.S. Application Data

[63] Continuation of Ser. No. 230,651, Aug. 5, 1988, abandoned, which is a continuation-in-part of Ser. No. 22,922, Feb. 26, 1987, abandoned.

[30] Foreign Application Priority Data

Mar. 12, 1986 [JP] Japan .................................. 61-53868
Feb. 17, 1987 [JP] Japan .................................. 62-32400

[51] Int. Cl.$^5$ ..................... C07D 273/06; A61K 31/55
[52] U.S. Cl. ..................................... 514/211; 540/547
[58] Field of Search ................. 514/217, 211; 540/547

[56] References Cited

U.S. PATENT DOCUMENTS 4,435,391  3/1984  Sasahara et al. ..................... 540/547

FOREIGN PATENT DOCUMENTS 0040860  2/1981  European Pat. Off. ............ 540/547

OTHER PUBLICATIONS

Wada et al., *Atherosclerosis*, vol. 40, No. 3-4, 1981, pp. 263-271.
Patent Abstracts of Japan, vol. 7, No. 259 (C-195), (1404), Nov. 18, 1983.
Patent Abstracts of Japan, vol. 6, No. 54 (C-97) (932), Apr. 9, 1982.
Patent Abstracts of Japan, vol. 6, No. 57 (C-98) (935), Apr. 4, 1982.
European Journal of Pharmacology, vol. 178, No. 2, 1990, pp. 255-258, Amsterdam, NL, M. Sugawa et al., "A Novel Dibenzoxazepine Derivative (BY-1949) Increases Regional Cerebral Blood Flow".

*Primary Examiner*—Frederick E. Waddell
*Assistant Examiner*—Zinna Worthington-Davis
*Attorney, Agent, or Firm*—Browdy and Neimark

[57] ABSTRACT

Disclosed is a therapeutic agent for the treatment of peripheral circulatory disorders that contains as the effective ingredient a dibenzoxazepin derivative of the following formula or a pharmaceutically acceptable salt thereof:

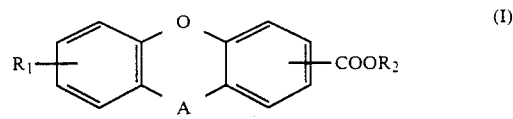

(I)

where $R_1$ is a hydrogen atom, a halogen atom, a lower alkyl group or a lower alkoxy group; $R_2$ is a hydrogen atom or a lower alkyl group; and A signifies the group

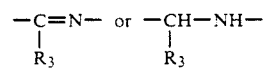

(where $R_3$ is a hydrogen atom, a lower alkyl group, an optionally substituted phenyl group or a styryl group). Also, disclosed is a method for treatment of peripheral circulatory disorders by administering the compound of the formula (I) or a pharmaceutically acceptable salt thereof to a patient suffering from such disorders.

3 Claims, 1 Drawing Sheet

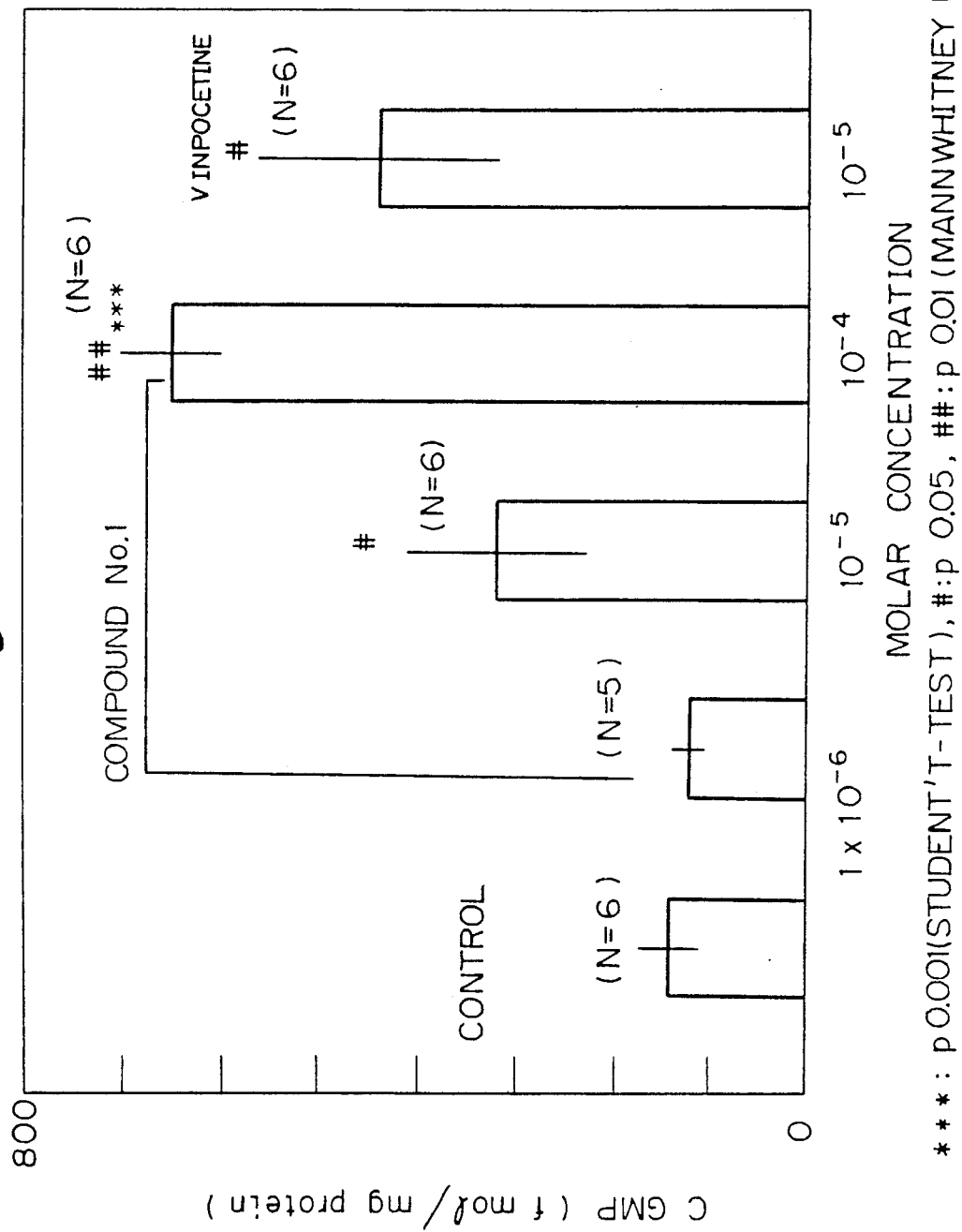

DIBENZOXAZEPINE COMPOUNDS USEFUL IN THE TREATMENT OF CEREBRAL VASOSPASM OR ITS SEQUELA

This application is a continuation of application Ser. No. 230,651, filed Aug. 5, 1988, now abandoned, itself a CIP of Ser. No. 07/022,922, filed Feb. 26, 1987, now abandoned.

BACKGROUND OF THE INVENTION a. Field of the Invention

The present invention relates to a therapeutic agent for the treatment of peripheral circulatory disorders that contains as the effective ingredient a dibenzoxazepin derivative of the following formula or a pharmaceutically acceptable salt thereof:

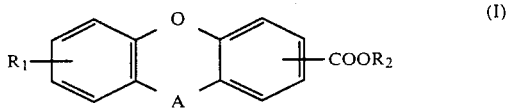

where $R_1$ is a hydrogen atom, a halogen atom, a lower group or a lower alkoxy group; $R_2$ is a hydrogen atom or a lower alkyl group; and A signifies the group

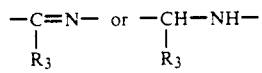

(where $R_3$ is a hydrogen atom, a lower alkyl group, an optionally substituted phenyl group or a styryl group).

b. Description of the Prior Art

The compounds of formula (I) were previously synthesized by the present inventors and their utility as medicines was seen to manifest not only by their ability to decrease lipids and peroxylipids, lower the blood sugar level and inhibit platelet aggregation (as shown in Japanese Patent Public Disclosure No. 166180/1981) but also by their ability to provide enhanced memory (as shown in Japanese Patent Public Disclosure No. 144319/1983).

SUMMARY OF THE INVENTION

A variety of therapeutic agents have been proposed or the treatment of cerebral circulatory disorders but many of them are rapidly lost from the blood and become ineffective in a relatively short period of time. When administered perorally, the compounds of the present invention are absorbed very rapidly but are lost from blood circulation slowly so that they maintain stable levels in the blood for a relatively prolonged period of time after administration. The increase in the regional cerebral blood flow peaks 30 minutes after administration and the effectiveness of the compound is sustained for a subsequent period of at least 4 hours. Similar retention of the compound's effectiveness has been observed in intravenous administration and this indicates the utility of the compound in the treatment of cerebral circulatory disorders. The compound has also been found to be useful in the treatment of other peripheral circulatory disorders. The compounds of the present invention promote peripheral blood flow by their surprisingly strong promotion of smooth muscle relaxation in blood vessels. The present invention has been accomplished on the basis of these findings.

Conventionally, the pharmacological actions of therapeutic agents for the treatment of cerebral circulatory disorders are in most cases evaluated with test animals being anesthetized or subjected to artificial respiration after being immobilized with gallamine but these conditions are not always ideal for simulating the physiological state of living animals.

The present inventors therefore employed the hydrogen clearance method wherein unanesthetized and unrestrained cats, each having a platinum electrode embedded in the cerebral cortex at four points, i.e., post. sigmoid G., post. sylvian G., mid. ecto-sylvian G. and post. suprasylvian G., and in the deeper area of the brain at three points, i.e., hippocampus, amygdala and hypothalamus, were exposed to a predetermined amount of hydrogen gas in a chamber. Using this method, the effects of compound Nos. 1 and 2 of the present invention on the regional cerebral blood flow (r-CBF) were evaluated. At the same time, analyses of blood pressure, the pH of blood, the gaseous components of the blood, and blood sugar levels were conducted with catheters being embedded in the femoral artery and vein.

Analyses by these methods showed that the compounds of the present invention have a great capability for increasing the peripheral blood flow and, hence, are useful as therapeutic agents for the treatment of peripheral circulatory disorders. They are particularly useful in ameliorating the symptoms of various peripheral circulatory disorders such as cerebral infarction or its sequela, cerebral hemorrhage or its sequela, cerebral apoplexy or its sequela, softening of the brain, cerebral edema, Buerger disease, Raynaud syndrome, intermittent claudication, presbyacusis, tinnitus and acute peripheral arterial embolism.

BRIEF DESCRIPTION OF THE DRAWINGS

FIG. 1 is a graph of cyclic GMP content vs. molar concentration of compound 1 and vinpocetine.

DETAILED DESCRIPTION OF THE PREFERRED EMBODIMENT

The daily dose of the therapeutic agent of the present invention when intended for the treatment of peripheral circulatory disorders ranges from 0.05 to 10 g, preferably from 0.2 to 3.0 g, for oral administration to an adult, and ranges from 0.01 to 2.0 g, preferably from 0.05 to 0.5 g for intravenous injection.

The compounds of the present invention are formulated in dosage forms suitable for peroral administration or injection by employing routine procedures. In preparing drugs for peroral administration, common auxiliary agents such as lactose, sucrose, sorbitol, mannitol, potato starch, corn starch, cellulose derivatives and gelatin may be advantageously used as vehicles, with magnesium stearate being simultaneously added as a lubricant. Alternatively, other lubricants such as carnauba wax and polyethylene glycol may be employed as required. A mixture of these ingredients may be formulated into various dosage forms such as granules, tablets and capsules by routine procedures.

In preparing aqueous formulations for injection, an effective amount of the drug or active principle is dissolved in distilled water for injection and, after an isotonic agent, a stabilizer, a local anesthetic, a preservative and any other necessary agents have been added, the mixture is given the necessary treatment to obtain a complete solution, which is filtered by a routine method and charged into ampules which are thereafter sealed and sterilized with steam. In preparing freeze-dried formulations for injection, an aqueous solution having the drug dissolved in distilled water for injection may be freeze-dried by a routine method. Alternatively, said aqueous solution may be mixed with an excipient that facilitates subsequent freeze-drying, such as sugar or sugar alcohol (e.g. mannitol, inositol, lactose, maltose or sucrose) or glycine, before it is freeze-dried by a routine method.

The following examples are provided for the purpose of further illustrating the present invention but are in no sense to be taken as limiting.

EXAMPLE 1

One month before the start of experiment, a platinum electrode was embedded in the cerebral cortex of Siamese cats (both female and male) at four points, i.e., post. sigmoid G., post sylvian G., mid. ecto-sylvian G. and post. suprasylvian G., and in the deeper area of the brain at three points, i.e., hippocampus, amygdala and hypothalamus, the cats being then exposed to a predetermined amount of hydrogen gas in a chamber in an unanesthetized and unrestrained state.

In order to evaluate the effects of compound Nos. 1 and 2 of the present invention on the regional cerebral blood flow (r-CBF), a predetermined amount of each test compound was administered either perorally (p.o.) in gelatin capsules or by intravenous injection (i.v.) In the latter case, 0.2 mg/kg or 1 mg/kg (body weight) of a selected compound of the present invention was dissolved in a quantity of physiological saline equivalent to 1 ml/kg (body weight) and the total amount of their solution was injected over a period of 10 minutes in a sustained manner through a cannula attached to a vein in the upper thigh; a control (vinpocetine) in an amount equivalent to 1 mg/kg or 5 mg/kg (body weight) was dissolved in a quantity of 10% ascorbic acid equivalent to 1 mg/kg (body weight) and the total amount of the solution was injected over a period of 10 minutes in a sustained manner through a cannula attached to a vein in the upper thigh.

Analyses of blood pressure, the pH of blood stream, the gaseous components of blood and blood sugar levels were also conducted, with catheters embedded in the femoral artery and vein.

In the r-CBF analysis, a clearance curve was obtained with a computer (Signal Processor 7T17, product of Nippon Electric Co., Ltd. and Sanei Co., Ltd.), transformed into semi-logarithmic values which were then processed by the initial slope method to calculate all the values of r-CBF. Only values having a coefficient of correlation of at least 0.9 for regression line were used as applicable data and the level of significance was determined by the paired-t test for absolute values, with the values before administration of a test compound being taken as a control. The level of significance for the control group was tested by time-series dispersion analysis. The results are shown in Table 1.

TABLE 1

| Compound No. | Route of administration | Dose (mg/kg) | Percent increase of r-CBF 30 min. | Percent increase of r-CBF 60 min. | Retention time (hr) |
|---|---|---|---|---|---|
| Control | p.o. | | −0.8 | 0.43 | |
| Vinpocetine | p.o. | 20 | 12.3 | 5.2 | <1 |
| 1 | p.o. | 10 | 12.9 | 14.4 | >4 |
| | p.o. | 20 | 11.8 | 11.0 | >4 |
| | p.o. | 50 | 14.6 | 10.0 | >4 |

TABLE 1-continued

| Compound No. | Route of administration | Dose (mg/kg) | Percent increase of r-CBF 30 min. | Percent increase of r-CBF 60 min. | Retention time (hr) |
|---|---|---|---|---|---|
| 2 | p.o. | 10 | 0.99 | 9.1 | <2 |
| | p.o. | 20 | 13.8 | 19.6 | >4 |
| | p.o. | 50 | 28.9 | 22.4 | >4 |
| Control (10% ascorbic acid) | i.v. | | −0.6 | 3.0 | |
| Vinpocetine | i.v. | 1 | 1.0 | <2.3 | — |
| | i.v. | 5 | −0.9 | 8.3 | <1 |
| Control (physiological saline) | i.v. | | −5.5 | −5.2 | |
| 1 (Na salt) | i.v. | 0.2 | 9.5 | 13.6 | <4 |
| | i.v. | 1.0 | 13.3 | 14.7 | >4 |
| 2 (Na salt) | i.v. | 0.2 | 12.1 | 21.0 | >4 |
| | i.v. | 1.0 | 8.1 | 10.0 | >4 |

The compounds of the present invention caused no pronounced variations in blood pressure, pH of the blood, the gaseous components of the blood or blood sugar levels at any point during the experiments.

EXAMPLE 2

(Experiment for acute toxicity)

Nos. 1, 2, 3 and 4 of the present invention were administered orally to 5-week old male CD-1 (ICR) mice and the $LD_{50}$ values (g/kg) were determined by a routine method. The results are shown in Table 2.

TABLE 2

| Compound No. | $LD_{50}$ (g/kg) |
|---|---|
| 1 | $3.5 > LD_{50} > 3.0$ |
| 2 | $5.0 > LD_{50} > 4.2$ |
| 3 | $3.4 > LD_{50} > 2.5$ |
| 4 | $3.2 > LD_{50} > 2.2$ |

EXAMPLE 3

(Formulation into dosage forms)

a) Granules

A drug (1,000 g), lactose (3,450 g) and carboxymethyl cellulose (500 g) were mixed intimately in a blender and were subsequently blended with 500 g of a 10% viscous solution of corn starch. The blend was granulated with a cylindrical granulator (0.7 mmφ) and subsequently dried with a box-type drier at 60° C. for 3 hours. The dried granules were classified by screening through a 14-mesh sieve.

b) Capsules

A drug (1,000 g), lactose (2,000 g), crystalline cellulose (750 g), carboxymethyl cellulose calcium (200 g), talc (30 g) and magnesium stearate (20 g) were charged into a V-type mixer and mixed for 15 minutes. The mixture was filled in No. 1 capsules using a capsule filling machine, with the contents of each capsule weighing 400 mg.

c) Tablets

A drug (1,000 g), lactose (540 g), crystalline cellulose (700 g), corn starch (250 g) and calcium stearate (10 g) were charged into a V-type mixer and mixed for 15 minutes. The mixture was subjected to direct compression with a rotary tableting machine equipped with deep concave punches (8 mmφ). Each of the tablets formed had a weight of 250 mg.

d) Injection

Aqueous preparation: Five grams of a drug (Na salt) and the necessary amount of NaCl were dissolved in distilled water for injection to make 1,000 ml (specific osmotic pressure: 1-3). The solution was filtered by a conventional method and charged into ampules such that each ampule contained 10 mg of the filtrate. The ampules were sterilized by autoclaving at 100° C. for 40 minutes.

Freeze-dried preparation: Five grams of a drug (Na salt) was dissolved in distilled water for injection and 50 g of mannitol was additionally dissolved to make 1,000 ml. The solution was aseptically filtered by a conventional method and charged into vials such that each vial contained 10 ml of the filtrate. The vials were freeze-dried by a conventional method, closed with a rubber stopper and sealed with an aluminum cap by routine methods. To use this preparation, it is dissolved in physiological saline as required.

EXAMPLE 4

Sprague-Dawley male rats were killed by decapitation, and their thoracic aortae were rapidly removed and immersed in ice-cold Krebs-Henseleit Ringer solution. The blood vessel was cut into rings with a length of about 3 mm and the weight of each wet tissue of the rings was measured. The rings of blood vessels were incubated at 37° C. for 30 minutes in portions of Krebs-Henseleit Ringer solution containing compound No. 1 ($1 \times 10^{-6}$, $10^{-5}$ or $10^{-4}$M) and vinpocetine ($10^{-4}$M) under an atmosphere of 95% $O_2$ - 5% $CO_2$. Trichloroacetic acid (6%) was then added to the solution to stop the reaction and the cyclic-GMP content was determined by radioimunoassay method (YAMASA c-GMP Assay Kit).

As FIG. 1 shows, cyclic-GMP content in the thoracic aortae increased dose-dependently by addition of compound No. 1.

This result suggest compound No. 1 produces relaxation of the smooth muscle of the blood vessel by the increase in cyclic-GMP, and increases the blood flow.

EXAMPLE 5

Beagles of either sex weighing about 20 kg were anesthetized with i.v. administration of sodium phenobarbital (30 mg/kg) and were sacrificed by rapid exsanguination. After the brain was removed, the basilar artery was dissected out under magnification and was sectional in at 2- to 3-mm intervals. A segment was mounted in a chamber (which was maintained at 37°±1° C.) containing 5 ml of a buffer solution (120 mM NaCl, 4.5 mM KCl, 2.5 mM $CaCl_2$, 1.0 mM $MgCl_2$, 27.0 mM $NaHCO_3$, 1.0 mM $KH_2PO_4$, 0.01 mM disodium EDTA and 10.0 mM glucose) bubbled with 95% $O_2$ plus 5% $CO_2$ gas (pH 7.4±0.1). The segment was initially stretched at a tension of 400 mg for 1 hour with a force-displacement transducer (SB-1T, Nihon Kohden, Tokyo, Japan) during which time the buffer solution was changed several times. Experiments were started after the segment was stretched at a final tension of 3 g inasmuch as preliminary studies showed that this tension provided the optimum length. The total volume of agents never exceeded 25 μl or 5% of the chamber volume and experiments were done in the dark.

The results are shown in Table 3. Compounds No. 1 and No. 2 show vasorelaxating action of fasilar artery, but other compounds do not.

TABLE 3

| Compounds* | Vasorelaxation (mg) | Relative Potency |
|---|---|---|
| Comp. No. 1 | 250.0 | 49.02 |
| No. 2 | 5.1 | 1.00 |
| No. I | −20.5 | −4.02 |
| No. II | 0 | 0 |
| No. III | 0 | 0 |
| No. IV | 0 | 0 |
| No. V | 0 | 0 |

—: vasoconstriction
0: no effect
*: the drug concentration used was $1 \times 10^{-5}$ M

EXAMPLE 6

(Experiment for Subacute Toxicity)

Compounds No. 1, IV, VI and VII were administered orally to male rats (F344/crj) at doses of 500 and mg/kg body weight daily for 30 days and body weight gain were measured.

The result are shown in Table 4. In compound No. 1 treated rats there was a smaller restriction of increase of body weight.

TABLE 4

| Compound | Dose (mg/kg) | body weight gain (g) |
|---|---|---|
| CONTROL | | 202.0 ± 14.9 |
| Comp. No. 1 | 500 | 191.8 ± 13.9 |
| | 2000 | 193.4 ± 13.4 |
| Comp. No. IV | 500 | 172.6 ± 8.2 |
| | 2000 | 124 (4/6 death) |
| Comp. No. VI | 500 | 193.7 ± 5.3 |
| | 2000 | 185.0 ± 7.6 |
| Comp. No. VII | 500 | 154.6 ± 10.4 |
| | 1000 | 168 (5/6 death) |

The chemical structures of compounds No. I–VII

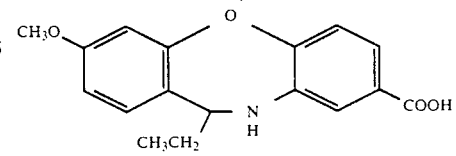

| Compounds | $R_1$ | $R_2$ | $R_3$ |
|---|---|---|---|
| Comp. | | | |
| No. I | OH | H | $CH_2CH_3$ |
| No. II | $CH_3$ | $CH_2CH_3$ | H |
| No. III | $OCH_3$ | $CH_2CH_3$ | $C_8H_5$ |
| No. IV | $OCH_3$ | $CH_2CH_3$ | $CH_2CH_3$ |
| No. VI | $CH_3$ | $CH_2CH_3$ | $CH_2CH_3$ |
| No. VII | $CH_3$ | H | $CH_2CH_3$ |

*The chemical structure of compound No. V

EXAMPLES OF SYNTHESIS

Reference Example 1

One gram of ethyl 3-methoxy-11-methyldibenzo[b,f][1,4]oxazepin-8-carboxylate was dissolved in 10 ml of methanol. To the solution, 10 ml of 1N sodium hydroxide was added and the mixture was refluxed for 1 hour. After cooling, the mixture was neutralized with dilute hydrochloric acid and the precipitating crystal was recovered by filtration. Recrystallization from methanol produced 0.84 g of 3-methoxy-11-methyldibenzo[b,f][1,4]oxazepin-8-carboxylic acid (Compound No. 1). Yield, 92%; melting point, 247° C. (with decomposition).

Elemental analysis for $C_{16}H_{13}NO_4$ Calcd. (%): C 67.84, H 4.63, N 4.94 Found (%): C 67.82, H 4.61, N 4.90

This Compound No. 1 was dissolved in an aqueous solution of sodium hydroxide and subsequently processed by routine manner to prepare a sodium salt of 3-methoxy-11-methyldibenzo[b,f][1,4]oxazepin-8-carboxylic acid.

Reference Example 2

The method of Reference Example 1 was repeated to prepare 3-methoxy-11-methyldibenzo[b,f][1,4]oxazepin-8-carboxylic acid (Compound No. 2). Melting point, 248°–250° C.

Elemental analysis for $C_{17}H_{15}NO_4$ Calcd. (%): C 68.68, H 5.09, N 4.71 Found (%): C 68.59, H 5.05, N 4.76

This Compound No. 2 was treated according to the method cited in Reference Example 1 to obtain a sodium salt of 3-methoxy-11-ethyldibenzo[b,f][1,4]oxazepin-8-carboxylic acid.

What is claimed is:

1. A therapeutic method for relaxing smooth muscle and increasing cerebral blood flow in the treatment of a cerebral vasospasm on its sequala which comprises administering to a person in need of said therapy an effective amount of a compound of the following formula or a pharmaceutically acceptable salt thereof:

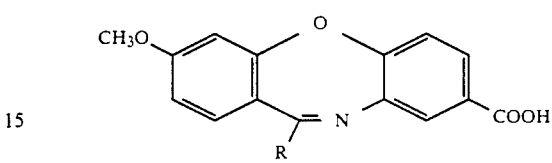

where R is methyl or ethyl.

2. A method according to claim 1, wherein said effective amount ranges from 0.05 to 10 g per day adult for oral administration and from 0.01 to 2.0 g per day per adult for intravenous injection.

3. A method according to claim 2, wherein said amount ranges from 0.2 to 3.0 g for oral administration and from 0.05 to 0.5 g for intravenous administration.

* * * * *